(12) United States Patent
Tsui et al.

(10) Patent No.: US 6,339,958 B1
(45) Date of Patent: Jan. 22, 2002

(54) ADHESION STRENGTH TESTING USING A DEPTH-SENSING INDENTATION TECHNIQUE

(75) Inventors: Ting Y. Tsui, Palo Alto; Young-Chang Joo, Sunnyvale, both of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/208,843

(22) Filed: Dec. 10, 1998

(51) Int. Cl.$^7$ ................................................. G01N 3/24
(52) U.S. Cl. .......................................... 73/150; 73/827
(58) Field of Search .......................... 73/150 A, 150 R, 73/827, 842, 105; 250/306, 307

(56) References Cited

U.S. PATENT DOCUMENTS

| | | | |
|---|---|---|---|
| 4,856,326 A | * 8/1989 | Tsukamoto | 73/150 A |
| 5,027,650 A | * 7/1991 | Oblas et al. | 73/150 A |
| 5,438,863 A | * 8/1995 | Johnson | 73/54.02 |
| 5,673,586 A | * 10/1997 | Mann | 73/150 A |
| 5,696,327 A | * 12/1997 | Huang et al. | 73/845 |

OTHER PUBLICATIONS

Ahn, J. et al., "Hardness and Adhesion of Filmed Strcutures as Determined by the Scratch Technique," Adhesion Measurement of Thin Films, and Bulk Coatings, ASTM STP 640, pp. 134–157 (1978).
Oroshnik, J. et al., "Threshold Adhesion Failure: An Approach to Aluminum Thin–Film Adhesion Measurement Using the Stylus Method," Adhesion Measurement of Thin Films, Thick Films, and Bulk Coatings, ASTM STP 640, pp. 158–183 (1978).
Brown, H.R., "Mixed–Mode Effects on the Toughness of Polymer Interfaces," Journal of Materials Science, vol. 25, pp. 2791–2794 (1990).
Xiao, F. et al., "Phase Angle Effects on Fracture Toughness of Polymer Interfaces Reinforced with Block Copolymers," Macromolecules, vol. 27, No. 15, pp. 4382–4390 (1994).
Xu, G., et al., "Measurement of the Fracture Energy of $Sio_2$TiN Interfaces Using the Residually–Stressed Thin–Film Micro–Strip Test," Materials Research Society, vol. 458, pp. 465–470 (1997).
Smith, J.W., et al., "Measurement of the Fracture Toughness of Polymer–Non–Polymer Interfaces," Journal of Material Science, vol. 28, pp. 4234–4244 (1993).

(List continued on next page.)

*Primary Examiner*—Hezron Williams
*Assistant Examiner*—Michael Cygan
(74) *Attorney, Agent, or Firm*—Foley & Lardner (57) ABSTRACT

A nanoindentation apparatus is used to measure adhesion strength of a hard, thin film to a soft substrate. A variably increasing load is applied to the indenter tip. The indenter tip penetrates into the thin film at a first penetration rate and causes the thin film to sink into the substrate thus causing a tensile stress at the film substrate interface. At a critical value of the applied load, the stress at the interface exceeds the delamination value, and the thin film partially delaminates from the substrate. This causes the indenter tip to sink into the softer substrate at a sudden second, higher penetration rate. A sensor detects the applied load and the indenter tip penetration depth at this point. A computer flags the critical value of the applied load that corresponds to the increased penetration depth rate at the point of delamination of the film. The computer then calculates the critical stress required for delamination and the adhesion strength between the film and the substrate from the critical value of the applied load. The depth sensing indentation technique measurement may be carried out on a thin film integrated test element so as not to damage the rest of the thin film. The method allows non-destructive in-situ adhesion strength measurements for thin films and microelectronic devices.

7 Claims, 8 Drawing Sheets

OTHER PUBLICATIONS

Doerner, M.F., "Plastic Properties of Thin Films on Substrates as Measured by Submicron Indentation Hardness and Substrate Curvature Techniques," Journal of Material Research, vol. 1, No. 6., pp. 845–851 (1986).

Larsen, T.A., "A Study of the Mechanics of Microindentation Using Finite Elements," Journal of Material Research, vol. 7, No. 3, pp. 618–626 (1992).

Oliver, W.C., "Measurement of Hardness at Indentation Depths as Low as 20 Nanometres," Microindentation Techniques in Materials Science and Engineering, ASTM STP 889, pp. 90–108 (1986).

Dugdale, D.S., "Wedge Indentation Experiments with Cold–Worked Metals," Journal of the Mechanics and Physics of Solids, vol. 2, pp. 14–26 (1953).

Dugdale, D.S., "Cone Indentation Experiments," Journal of the Mechanics and Physics of Solids, vol. 5, pp. 265–277 (1954).

Oliver, W.C. et al., "An Improved Technique for Determining Hardness and Elastic Modulus Using Load and Displacement Sensing Indentation Experiments," Journal of Material Research, vol. 7, No. 6, pp. 1564–1583 (Jun., 1992).

Wu, T.W. et al., "Micro–Indentation and Micro–Scratch Tests on Sub–Micron Carbon Films," Materials Research Society Symposium Proceedings, vol. 130, pp. 117–122 (1988).

Marshall, D.B. et al., "Measurement of Adherence of Residually Stressed Thin Films by Indentation," Journal of Applied Physics, vol. 56, No. 10, pp. 2632–2638 (Nov., 1984).

Tsui, T.Y. et al., "Nanoindentation and Nanoscratching of Hard Coating Materials for Magnetic Disks," Materials Research Society Symposium Proceedings, vol. 356, (1994).

Tsui, T.Y. et al., "Effects of Adhesion on the Measurement of Thin Film Mechanical Properties by Nanoindentation," Materials Research Society Symposium Proceedings, vol. 473, pp. 51–56 (1997).

Anderson, T.L., "Fracture Mechanics: Fundamentals and Applications, 2nd Ed.," CRC Press, Ch. 12, pp. 601–608; Ch. 3, pp. 117–122, 178; Ch. 2, pp. 82–89; Ch. 12, pp. 610–626.

Y. Martin, C.C. Williams, and H. K. Wickramasinghe, published Jan. 26, 1987, Applied Physics vol. 61, pp. 4723–4729.*

* cited by examiner

ADHESION STRENGTH TESTING USING A DEPTH-SENSING INDENTATION TECHNIQUE

FIELD OF THE INVENTION

The present invention is directed to method and apparatus for testing adhesion strength between two materials using a depth sensing indentation technique.

DESCRIPTION OF RELATED ART

Thin films are very important in many applications. For example, thin films are used extensively in microelectronics applications where devices often have features of submicron size. Thin films are also used extensively in micromechanical applications for making devices such as microgears and accelerometers, and other applications such as for making hard disks in a hard drive and hard coating for gear boxes.

Determining the mechanical properties of thin films in these applications can be critical. For example, a thin film having a large tensile stress may delaminate causing device failure under certain conditions. The mechanical properties of a thin film material cannot be simply predicted based upon the properties of the bulk material for a number of reasons. The mechanical properties of the thin film will generally be different from that material in bulk form, and will depend upon the particular technique for forming the film, and the conditions under which the film is formed. For example, a thin film formed on a substrate at high temperature and then cooled to room temperature may exhibit either a tensile or compressive stress due to the difference in the coefficient of thermal expansion between the film and the substrate. Also a thin film may delaminate from a substrate due to stress applied by an outside source.

Figure 1:
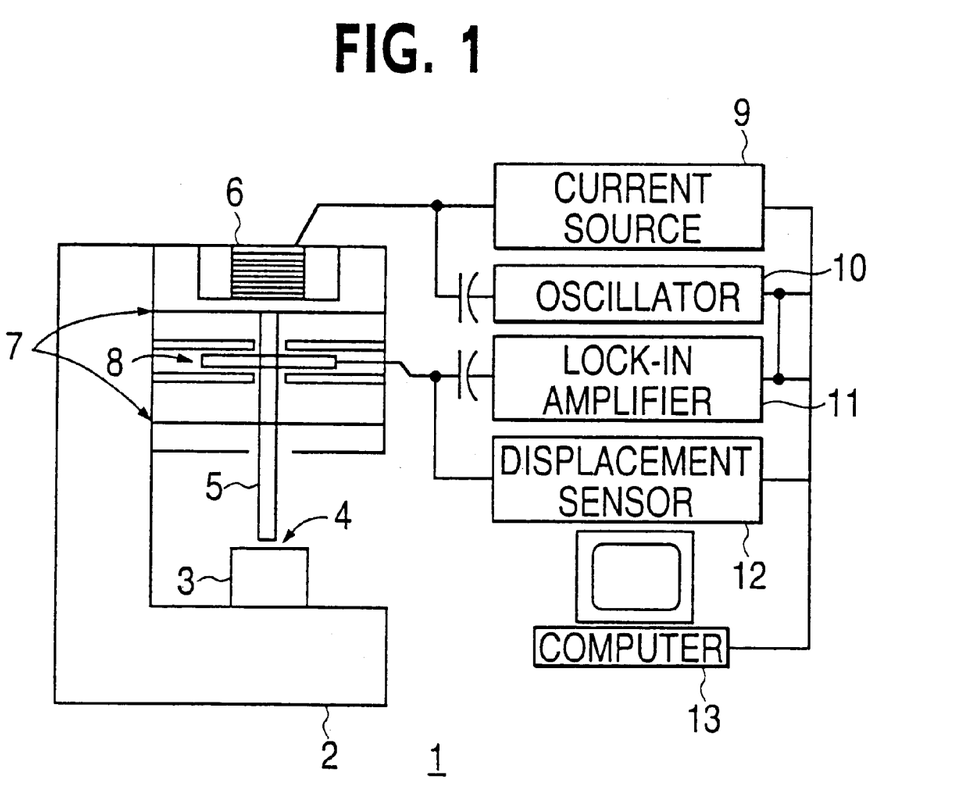
FIG. 1 is a schematic of a nanoindentation system.

Depth sensing techniques, such as nanoindentaion and microindentation techniques, have been used for measuring material hardness and elastic modulus of a material. One exemplary system for performing nanoindentation hardness measurements is shown in FIG. 1. The apparatus 1 contains a sample stage 2 on which the sample to be tested 3 is placed. The indenter tip 4 is situated above the sample 3. As an example, the indenter tip may be a sharp Berkovich type diamond indenter tip which has a three sided pyramid tip with a known area to depth correlation. The indenter tip 4 is supported by the indentation column 5 which is moved up and down by a load application coil 6. The apparatus also contains indentation column guide springs 7 and a capacitive displacement sensor 8. The load application coil is connected to a current source 9 and an oscillator 10, while the capacitive displacement sensor is connected to a lock-in amplifier 11 and an electronic displacement sensor 12. The electronics are controlled by a computer 13.

The prior art apparatus operates in the following manner. The computer sends a signal to lower the indenter tip 4 into the sample. The computer operator enters into the computer a desired maximum load on the indenter tip. The indenter tip can penetrate up to a certain maximum depth into the sample for a given maximum load. Of course, for each material, the maximum depth differs for a given load because each material has a different hardness. The maximum penetration depth of the indenter tip is monitored by the capacitive displacement sensor 8. As the indenter tip 4 penetrates further into the sample, the capacitive plate attached to the indentation column 5 moves closer to the capacitive plate attached to the sample stage 2. Therefore, the capacitance between the two plates changes. The change in capacitance is detected by the electronic displacement sensor 12 which forwards the data to the computer 13. The computer than correlates the maximum load applied to the maximum penetration depth. The oscillator and lock-in amplifier may be used to scan the indenter tip across the sample.

Sample hardness may be calculated from nanoindentation measurements using, for example, two different methods. The first method is a depth measuring method. In this method, the penetration depth of the indenter tip for a predetermined peak (maximum) load is measured by the indentation apparatus and the contact area (e.g., the area of the sample contacted by the indenter tip) is extrapolated from the known shape and geometry of the indenter tip. Then sample hardness is calculated as a function of penetration depth.

The second method is an imaging method. In this method, the peak load exerted by the indentation apparatus is preset and the contact area is determined by an optical or electron microscopy examination. Sample hardness is determined from a ratio of the applied maximum load applied to the measured contact area.

Once hardness is calculated, the elastic modulus may be calculated from the hardness. The hardness may be calculated from a simple formula with a high error margin (See W. C. Oliver, R. Hutchins and J. B. Pethica, "Measurement of Hardness at Indentation Depths as Low as 20 nanometers," *Nanoindentation Techniques in Materials Science and Engineering*, ASTM STP 889, P. J. Blau et al. eds., ASTM (1986) pp. 90–108, incorporated herein by reference) or from finite element analysis calculations using the unloading portion of a load displacement curve with a low error margin (See W. C. Oliver and G. M. Pharr, *J. Mater. Res.* Vol. 7, No. 6 (1992) pp. 1564–83 and T. A. Laursen and J. C. Simo, *J. Mater. Res.* Vol. 7, No. 3(1992) pp. 618–26, both incorporated herein by reference). The sample may be a bulk sample or it may be a film on a substrate. Thus, hardness of a film may be measured by nanoindentation techniques.

Despite the different calculation techniques, hardness measurements in the prior art utilize a predetermined maximum load. In other words, the user selected a certain value of the maximum load, then this maximum load was applied to the sample, the penetration depth or contact area were measured, and hardness was calculated.

In addition, the prior art adhesion testing methods require destructive testing of the adhered materials. For example, in one prior art method, a representative article containing a film adhered to a substrate would be selected during mass production and pulled apart from the substrate by a layer of glue attached to the film. However, this stud pull method requires a large testing area and is expensive and time consuming. It also cannot be used to test the adhesion strength of all articles actually used or sold to the customers. Thus, even if adequate adhesion strength between materials was measured on the test article, other articles sold to customers or used by the manufacturer could easily have inadequate adhesion strength between adhered materials. Furthermore, the stud pull test cannot be properly used for thin films, such as those thinner than a thousand microns.

A second prior art method of adhesion testing is the blister test, where a hole is made in the substrate and then liquid or air pressure is applied through the hole to bulge the film outward. This method has the same disadvantage as the above-noted stud pull test. This method is also cumbersome and destructive.

A third prior art method of adhesion strength testing is the scratch test, where the film is scratched until it delaminates from the substrate. Such a method is taught, for example, by T. W. Wu et al., MRS Symp. Proc., Vol. 130 (1989) page 117, and in *Adhesion Measurement of Thin Films, Thick Films and Bulk Coatings*, K. L. Mittal, ed., ASTM (1978), pages 134–183, both incorporated herein by reference. In this method, a indenter tip is dragged across a thin film under an increasing load until the film delaminates from the substrate. The critical load for delamination is determined from an onset of a drop in the load. However, this method damages a significant portion of the film under investigation. This method also is subject to inaccuracies, because the drop in the load may be caused by flaking of the thin film instead of by delamination of the film from the substrate. Since for certain brittle thin films the onset of flaking precedes the delamination, the adhesion strength of such thin films cannot be accurately determined by the scratch test.

SUMMARY OF THE INVENTION

One object of an embodiment of the present invention is a nondestructive depth sensing indentation adhesion strength measurement method that avoids the above mentioned problems of destructive testing methods. The adhesion strength between parts of each article under production may be tested according to the method of an aspect of the current invention without the device being rendered inoperable.

Another object of an embodiment of the present invention is to form a film on a substrate and to determine its adhesion strength to the substrate by using a depth sensing indentation technique, such as nanoindentation.

A further object of an embodiment of the present invention is to utilize a depth sensing indentation apparatus, such as a nanoindentation apparatus, to measure a property of a material other than hardness or elastic modulus, such as adhesion strength of the material to a substrate.

Yet another object of an embodiment of the present invention is to perform in-situ measurement of adhesion strength of materials undergoing processing without requiring expensive and inconvenient ex-situ destructive testing.

Yet a further object of an embodiment of the present invention is an integrated test element formed on a substrate along with a thin film. The integrated test element may be used to test adhesion strength of the film to a substrate without damage to the film.

In accordance with an aspect of the present invention, there is provided a method of forming a thin film comprising forming a film on the substrate, forming a nanoindentation in at least the film and determining the adhesion strength of the film to the substrate. Furthermore, the film is rejected if the adhesion strength of the film to the substrate is below a desired value and the film and the substrate are processed further if the adhesion strength of the film to the substrate is equal to or above a desired value.

In accordance with another aspect of the present invention, there is provided a method of determining adhesion strength between two materials comprising forming a nanoindentation in one material and calculating the adhesion strength between the two materials. Furthermore, the first material is preferably a thin film and the second material is preferably a substrate.

In exemplary embodiments of the present invention, the depth sensing measurement is performed by pressing an indenter tip into the first material under a variable applied load while monitoring the applied load and penetration depth of the indenter tip. The load is increased with time and the indenter tip penetrates into the first material. The increasing load causes the indenter tip and the first material to "sink in" the second material. The first material at least partially delaminates from the second material under the increasing load, and the indenter tip "sinks in" the second material at a greater penetration depth rate than the penetration depth rate prior to the time the first material at least partially delaminates from the second material. An increase in the penetration depth rate and a critical value of the applied load at the time of the increase in the penetration depth rate are detected. A critical stress required to at least partially delaminate the first material from the second material is then calculated from the detected value of the critical value of the applied load. Finally, the adhesion strength between the first material and the second material is calculated from the critical stress.

In accordance with another aspect of the present invention, an apparatus for adhesion strength testing comprises an indenter tip, means for applying a variable load to the indenter tip, means for monitoring a penetration depth of the indenter tip into a sample, and means for calculating adhesion strength of a first part of the sample to a second part of the sample. Preferably, the apparatus also contains means for detecting a change in the penetration depth rate and means for detecting a critical value of the applied load at the time of the change in the penetration depth rate. In accordance with the present invention, the apparatus is used to calculate the adhesion strength of a first part of a sample to a second part of the sample.

In accordance with one embodiment of the present invention, there is provided a method of testing adhesion strength of a thin film to a substrate. The thin film and the substrate may comprise any of various materials. According to the present invention, the substrate may comprise either a base material or at least one intermediate film formed on a base material. The substrate may be at least one of a semiconductor device, an integrated circuit, a metal layer, an insulating layer, a gear box, a micromechanical device, a liquid crystal display, an electron emissive cathode substrate and a magnetic disk. A micromechanical device may comprise an air bag activation system or a solid state accelerometer.

According to the present invention, the thin film may comprise a single layer or a plurality of layers. The thin film may be at least one of metal film, an electrode for a semiconductor device, an interconnection for an integrated circuit or a liquid crystal display, a gear box coating, a magnetic disk overcoat, an electron emissive cathode and a micromechanical device portion. Preferably, the thin film thickness is 5 microns or less, and preferably, the thin film element being tested has a limited or finite width. The thin film test element can have any shape when viewed from the top, such as a linear strip, a rectangle, a square, a circle or an oval.

In accordance with another embodiment of the present invention, the thin film contains a first portion and a second portion, wherein the first portion is an integrated test element. Preferably, the integrated test element is not in physical contact with a second portion of the thin film. The integrated test element is used to test the adhesion strength of the film to the substrate during processing of the film without damaging the second portion of the film. The integrated test element contains a nanoindentation therein, and is preferably at least partially delaminated from the substrate after the adhesion strength testing is carried out.

In accordance with one aspect of this embodiment, the integrated test element is formed in an integrated circuit. The integrated test element allows in-situ adhesion strength testing of each layer of integrated circuit metallization to an underlying layer without removing the circuit wafer from a multichamber apparatus.

In accordance with another aspect of this embodiment, more than one thin film and more than one integrated circuit elements are formed. The plural integrated test elements allow adhesion strength testing of the first thin film to the substrate as well as the adhesion strength testing of the second thin film to the first thin film, and so on.

In accordance with another embodiment of the invention, sacrificial spacers are formed under the edges of a thin film test element. Removal of the sacrificial spacers speeds up delamination of the test element from the substrate during adhesion strength testing.

The term "depth sensing indentation technique," as used herein, refers not only to nanoindentation measurements, but also to various other depth sensing methods, such as Rockwell Hardness Testing method. The term "nanoindentation," as used herein, includes microindentation within its scope, and refers to a relatively small indentation in a material, and is not meant to be limited to indentations that have dimensions measured in nanometers. Furthermore, nanoindentation is formed by lowering an indenter tip or stylus down into the sample without dragging or moving it across the surface of the sample, as is common in the scratch test.

DETAILED DESCRIPTION OF THE PREFERRED EMBODIMENTS

One nanoindentation apparatus that may be used to determine the interfacial strength between the film and the substrate is similar to the one shown in FIG. 1 and described above. One such apparatus is sold under the trademark "Nanoindenter" by Nano Instruments of Knoxville, Tenn. Any other known nanoindentation apparatus may be used. However, to carry out the method of the present invention, the apparatus is configured to operate differently than the previous apparatuses used to measure material hardness. The user does not enter a particular maximum applied load. Instead, the computer continuously increases the load on the indenter tip. The indenter tip penetrates into the sample to a certain depth in response to each applied load. The penetration depth and penetration depth rate are monitored by the capacitive displacement sensor 8 and the electronic displacement sensor 12. The detected penetration depth is continuously transferred to a data processor, such as computer 13, which correlates each value of the load applied with a value to the measured penetration depth and penetration depth rate. The computer then determines the critical (delaminating) load based on the measured values of the penetration depth and its rate. The computer then calculates the critical (delaminating) tensile stress and adhesion strength between constituent parts being tested (e.g. delaminating of a film from a substrate) from the calculated value of the maximum load. Also, the oscillator and lock-in amplifier may be omitted from the apparatus of the present invention.

One method of calculating adhesion strength from a value of the critical load is to approximate adhesion strength between two materials as a shear force required for delamination, F:

$$F=(A*P)/(R^2-A^2)^{0.5}$$

Where P is the indentation hardness of the material being tested, R is the radius of the indenter tip and A is:

$$A=(L_c/(\pi*P))^{0.5}$$

Where $L_C$ is the critical load. Tensile stress can be similarly calculated from a value of the critical load.

Other adhesion strength calculation methods may also be used. For example, the adhesion strength can be approximated as fracture toughness, κ or as energy required to delaminated an area of a sample. The fracture toughness may be calculated from the geometry of the crack using finite element analysis. For example, the length and shape of a crack between thin film and the substrate after delamination of the thin film may be imaged by an atomic force microscope (AFM). The fracture toughness and adhesion strength may then be calculated from the length and shape of the crack using finite element analysis techniques that are well known in the art. See for example, Lausen et al., "A study of the mechanics of microindentation using finite elements", J. Mater. Res., Vol. 7, No. 3, March 1992, pp. 618–626, which is herein incorporated by reference. The finite element analysis may be performed using a computer with software such as ANSYS, which is sold by ANSYS, Inc.

Alternatively, the adhesion strength can be approximated by the so called "J contour integral." For example, thin film delamination from the substrate can be modeled as a rotation of a cracked plate in plane strain subject to combined bending and tension. In this model, the edges of the thin film can be modeled as rotating with a moment, M, about the point in the thin film where the indenter tip penetrates. The J contour integral is a function of the moment M and crack geometry. The moment M may be determined from the critical load, $L_C$, while the crack geometry may be determined by AFM imaging. This method is described in *Fracture Mechanics*, T. L. Anderson, Second edition, CRC Press, page 622, which is incorporated herein by reference.

FIGS. 2A to 2E show a method for carrying out the current invention. FIGS. 3A to 3E show a plot of penetration depth versus applied load for each stage shown in FIGS. 2A to 2E.

Figure 2A:
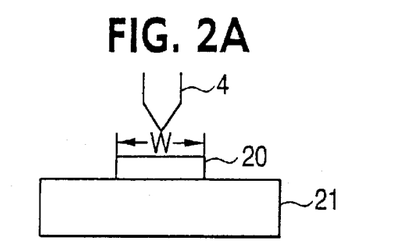
FIGS. 2A to 2E are cross sectional views of a method of measuring adhesion strength according to the present invention.
Figure 3A:
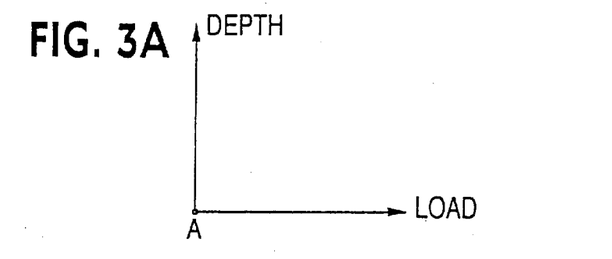
FIGS. 3A to 3E are plots of penetration depth versus applied load that correspond to the situations depicted in FIGS. 2A to 2E above.

In FIG. 2A, a test sample is shown. The test sample is preferably a thin film strip 20 of a material having a limited or finite width, W, on a substrate 21. Preferably, the width W is several times greater than the width of the indenter tip and large enough so that film 20 may be detected. The width, W, depends on the curvature of the film and the substrate, as well as on the stiffness of the film and substrate material. The width should be selected so as to allow at least a partial delamination of the strip from the substrate during the depth sensing (e.g. nanoindentation) measurement. The film may be shaped as a square or rectangle or any other appropriate shape when viewed from the top. The film 20 is preferably harder than the substrate 21. It should be understood that the substrate may be a bulk substrate or another thin film deposited on other film(s) or another substrate. The indenter tip 4 is positioned above the film 21. Preferably, the indenter tip is a Berkovich type indenter tip, but other known indenter tips can be used. In FIG. 3A, the applied load and the penetration depth are both equal to zero.

Figure 2B:
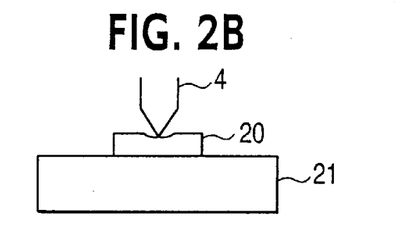
Figure 2C:
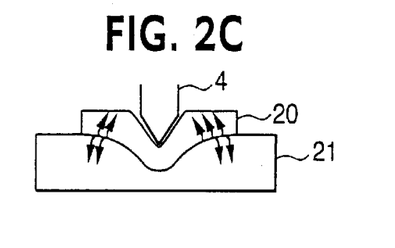
Figure 3B:
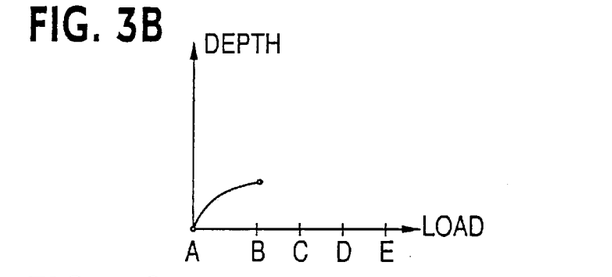
Figure 3C:
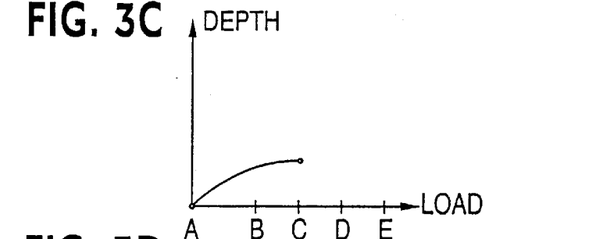

In FIG. 2B, the indenter tip penetrates slightly into the film at load B, causing the film to compress at the point of contact. In FIG. 3B, the penetration depth increases with increased load. In FIG. 2C, the indenter tip penetrates deep into the film at load C, causing the film to further compress at the point of contact and the substrate begins to compress below the film. This is referred to as the "sinking in" effect. The load also causes a Mode I interfacial tensile stress between the film and the substrate at the edge of the film, as shown by the arrows. In FIG. 3C, the penetration depth further increases with increased load, though at a lower rate.

Figure 2D:
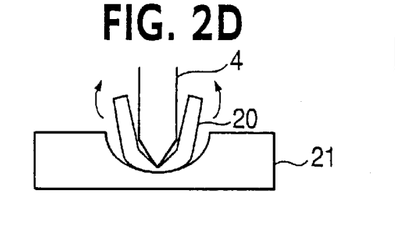
Figure 2E:
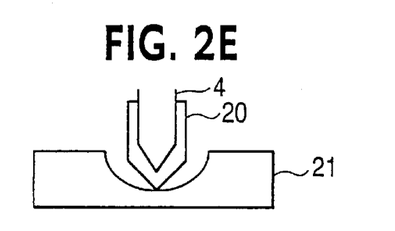
Figure 3D:
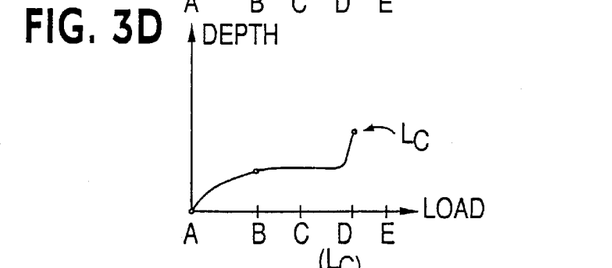
Figure 3E:
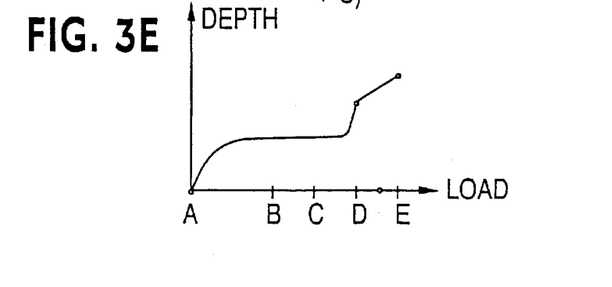

In FIG. 2D, the load D creates a tensile stress at the film substrate interface greater than the critical (delaminating) stress. The film delaminates from the substrate at the edges, creating a Mode I opening. Since the harder film no longer resists penetration by the indenter tip, only the softer substrate impedes the penetration of the indenter tip. This sudden decrease in resistance to penetration causes the indenter tip to suddenly, rapidly sink deeper into the softer substrate. In FIG. 3D, there is a sudden increase in penetration depth at critical load, $L_C$, at point D and a corresponding sudden increase in the indenter tip penetration rate. A sudden increase in the penetration depth rate is a relatively large change in the penetration depth rate over a relatively short period of time. After the film delaminates, increasing the load causes the indenter tip to penetrate further into the substrate, as shown in FIGS. 2E and 3E. It is preferred that the indenter tip is applied as close as possible to the center of the film segment being tested.

Figure 4:
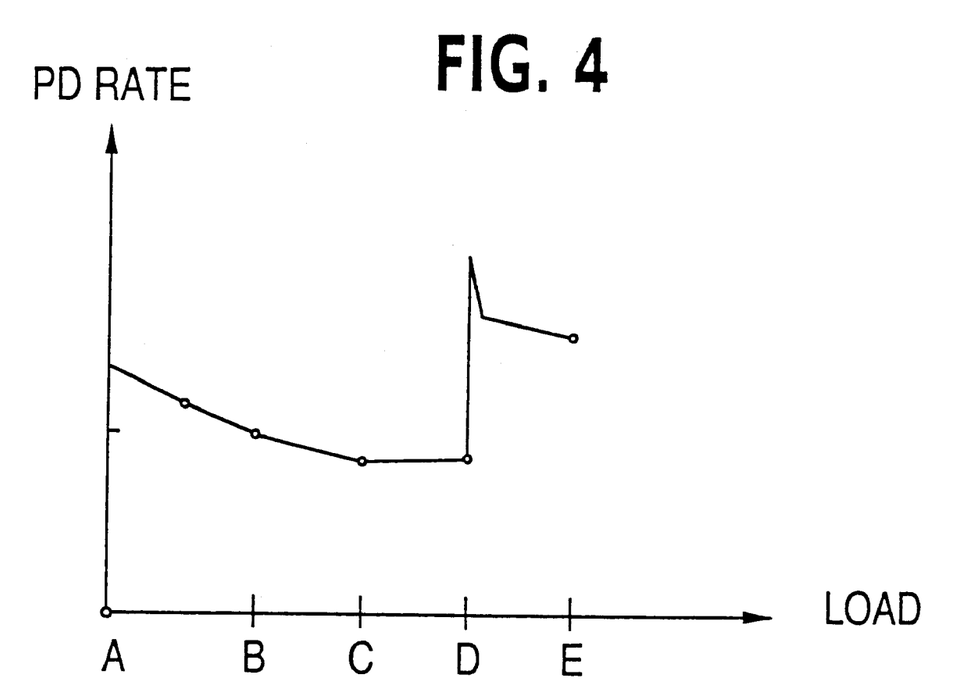
FIG. 4 is a plot of penetration depth rate versus the applied load used to determine adhesion strength according to a method of the present invention.

The penetration rate is plotted against the applied load in FIG. 4; Loads at points A,B,C,D and E in FIG. 4 correspond to the loads shown in FIGS. 3A–E, respectively. The rate slightly decreases for loads between points A and D due to the film resistance effects. The rate suddenly increases at critical load $L_C$ at point D due to the delamination of the film, because at this point, only the softer substrate provides resistance to the indenter tip penetration instead of a composite of the harder film and the substrate. The penetration rate in the range between D and E decreases due to the substrate material effects. Therefore, the critical load may be easily detected by flagging the corresponding sudden increase or spike in the penetration rate.

Figure 5A:
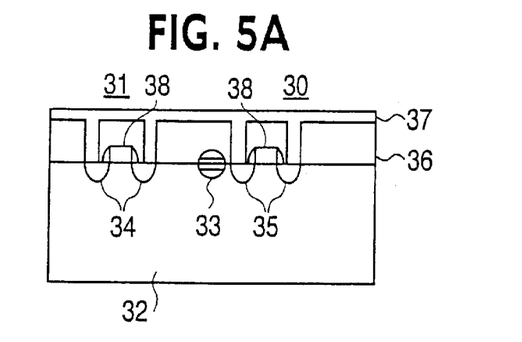
FIGS. 5A to 5D are cross sectional views of an adhesion strength measurement according to an embodiment of the present invention applied to an integrated circuit.

FIGS. 5A to 5E show another embodiment of the present invention where the depth sensing indentation technique adhesion strength measurement is utilized in an integrated circuit. For example, FIG. 5A shows a CMOS, which is a typical semiconductor device used in microprocessors and memory devices. The CMOS contains a first MOSFET 30 and a second MOSFET 31 on a semiconductor substrate 32. The MOSFETs 31 and 32 are separated by a field insulation layer 33. Each MOSFET contains doped source and drain regions 34, 35, and a gate structure 38. The CMOS is covered by a first insulating layer 36, commonly referred to as an interlayer insulating layer. Insulating layer 36 may comprise a single insulating layer, such as any of silicon dioxide, silicon nitride, silicon oxynitride, spin-on glass (SOG), doped silicon oxide (BPSG, PSG), polymers and other films. Alternatively, insulating layer 36 may comprise a plurality of insulating films selected from the group above, as well known in the art. Via holes in the insulating layer 36 are opened by a method such as photolithography and etching. A first metal layer 37 is then deposited over the first insulating layer 36. The first metal layer may comprise any metal known in the manufacture of solid state devices. For example, the first metal layer may comprise Al, Cu, Ti, W, Co, polysilicon, TiN, WSi, TiSi, noble metals and their silicides or other metal layers. Alternatively, first metal layer may comprise a plurality of metal layers, such as TiSi/TiN/Al stack. The first metal layer may be deposited by any known technique, such as CVD, sputtering, evaporation and plating. Metal layer 37 fills in the via holes in insulating layer 36 to contact the source and drain regions 34,35 of the MOSFETs.

Figure 5B:
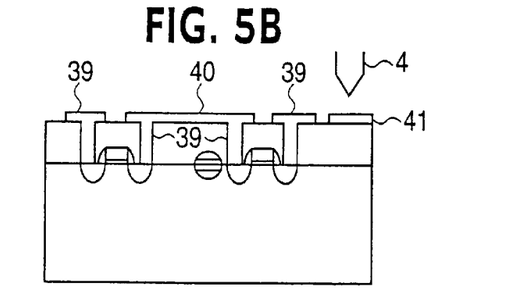

In FIG. 5B, the metal layer 37 is patterned by photolithography and etching to form electrodes 39, which contact the source and drain regions 34,35, an interconnection layer 40 that connects the drain electrode of the second MOSFET 31 to the source electrode of the first MOSFET 30, and an integrated test element 41. Thus, the integrated test element 41 is formed during the same photolithography and etching step used to pattern the electrodes and/or interconnection. That is, no additional photolithography and etching operations are required to form the integrated test element 41. The integrated test element 41 corresponds to the thin film strip 20 of FIG. 2A. The integrated test element 41 has the same adhesion strength to the insulating layer 36 as the adhesion strength of electrodes 39 and interconnection layer 40 because they were originally part of the same metal layer 37. Therefore the integrated test element 41 may be used to accurately test the adhesion strength of electrodes 39 and interconnection layer 40 to the insulating layer 36.

Due to process non-uniformity during deposition, the metal layer 37 may have poor adhesion to insulating layer 36, leading to the delamination of electrodes 39 and interconnection 40 from the insulating layer 36 under stress during subsequent processing. Therefore it is desirable to in-situ test the adhesion strength of the electrodes and interconnections to the underlying insulating layer prior to carrying out further processing. An indenter tip 4 is aligned over the integrated test element 41 by methods similar to those used in the photolithography art, and a depth sensing indentation technique adhesion strength test is carried out by the method described above in connection with FIGS. 2–4. If the adhesion strength determined by the depth sensing indentation method is below a predetermined required adhesion strength, then the entire semiconductor substrate (e.g. wafer) 32 may be discarded. Semiconductor devices cannot properly operate with delaminated metal layers. Thus, if the adhesion strength of the metal layers is below the required strength, the metal layers will probably delaminate during subsequent processing, causing an inoperative integrated circuit. By testing the metal layer adhesion strength prior to subsequent processing, and discarding wafers with poorly adhered metal layers, the cost associated with the subsequent processing may be avoided.

Figure 5C:
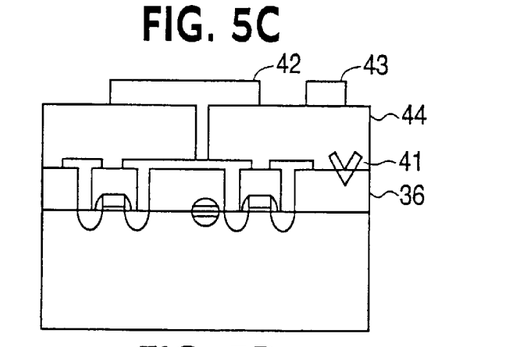

FIG. 5C shows the next step in forming an integrated circuit. The integrated test element 41 has been partially delaminated from the underlying insulating layer 36 during the depth sensing indentation adhesion strength testing. However, since the integrated test element 41 is formed in the corner of the wafer, no other layers or regions were affected or destroyed during the testing. Therefore, the depth sensing indentation adhesion strength test is non-destructive. A second interlayer insulating layer 44 is formed over the electrodes 39, interconnection 40 and test element 41. Via holes are again patterned in the insulating layer 44. A second layer of metal is then deposited and patterned to form a second interconnection 42 and a second integrated test element 43. A second depth sensing indentation adhesion strength test is then carried out on test element 43. The adhesion strength of test element 43 is the same as that of interconnection 42. Thus, if the adhesion strength of test element 43 is below some predetermined required value, the whole wafer may be discarded because interconnection 42 is likely to delaminate during subsequent processing. Again, the depth sensing indentation test is non-destructive because no elements others than test element 43 formed on the corner of the wafer are damaged. It is further noted that the damaged test elements 41 and 43 do not affect the performance of the integrated circuit because they are made at the periphery of the wafer.

Figure 5D:
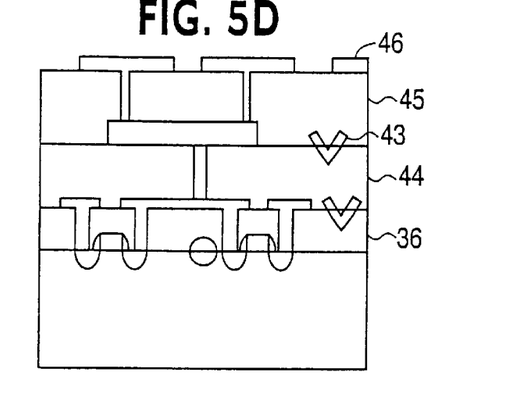

A third interlayer insulating layer 45 is then deposited on interconnection 42 and test element 43, a new integrated test element 46 is formed and the process described above is repeated once again. The steps may be repeated for some or all levels of metallization. Thus, if the there are six metallization layers, the depth sensing indentation process may be performed up to six times. Another advantage of the present in-situ depth sensing indentation adhesion strength measurement becomes apparent. In the previously described methods, adhesion strength was not measured in-situ because it required a destructive test. Therefore, testing could not be performed until the integrated circuit was finished. However, certain metal layers with inadequate adhesion strength may have survived subsequent processing without delaminating. The electrical testing after the integrated circuit is complete is unable to detect this defect in the integrated circuit. Such an integrated circuit with a poorly adhered metal layer may then unexpectedly fail during routine end use. For example, the integrated circuit may be used in an environment that subjects it to physical stresses (e.g. lap top computer, cellular phone, automobile computers, etc.). In this case, routine use of the device containing the integrated circuit may cause the integrated circuit to unexpectedly fail due to metal delaminating and render the device useless. The method of the current invention allows adhesions strength testing of all metal layers before they are sealed in chip package. Thus, the likelihood of unexpected failure of an electronic device, that contains an integrated circuit formed by the method of the present invention, due to physical stress is reduced.

Figure 6:
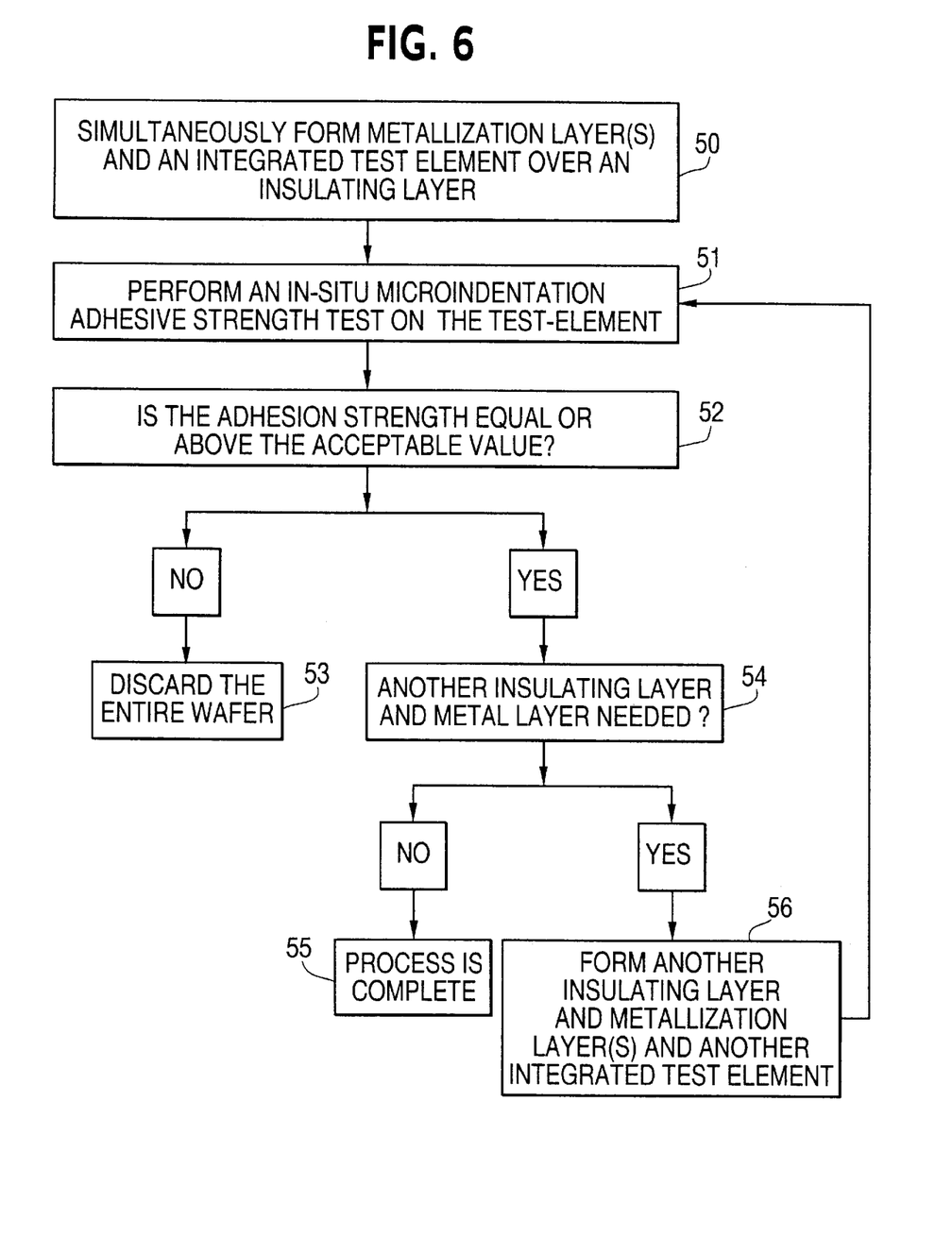
FIG. 6 is a flow chart for carrying out the method of the present invention applied to an integrated circuit.

FIG. 6 shows a flow chart for carrying out the method of depth sensing indentation technique strength testing on an integrated circuit. In block 50 the metallization layer(s), such as electrodes and interconnections, are simultaneously formed with the integrated test element, as shown in FIG. 5B. In block 51, a depth sensing indentation technique adhesion strength test is performed on the test element using the general apparatus of FIG. 1 and the method shown in FIGS. 2–4. Since integrated circuit manufacture is carried out in a multichamber apparatus under vacuum, an extra chamber containing the apparatus of FIG. 1 may be readily added to the known multichamber vacuum processing apparatus. Thus, the wafer containing the test element can be taken out from the metal deposition chamber by a robot arm, and carried through a vacuum passage to the chamber housing the depth sensing indentation technique apparatus. The testing apparatus would then test the adhesion strength of the test. In block 52, the computer shown in FIG. 1 determines if the adhesion strength of the test element is equal to or above an acceptable value that may be entered by the user, or is part of a software program, etc. If it is not, then the wafer is discarded from the vacuum chamber (block 53). If it is, then the computer checks if the test element is part of the final layer of metallization (block 54). If no more metal layers are needed, the robot arm takes the wafer into a first deposition chamber to put a final capping layer on the wafer, and the wafer is then removed from the multichamber apparatus (block 55). If more metal layers are necessary, the robot arm takes the wafer to a subsequent deposition chamber(s) to deposit additional insulating and metal layers (block 56). The metal layer is patterned to form a test element and the adhesion strength test is repeated (block 51). Thus, the entire fabrication and testing process may take place without breaking vacuum. It should be understood that the method described in the flow chart of FIG. 6 is not limited to integrated circuit processing and may be used to make any device or article of manufacture that requires deposition of several layers.

According to another embodiment of the present invention, the film may be an aluminum layer on glass or sapphire used as metallization in a liquid crystal display or thin film transistor. Preferably, the thin film thickness is 5 microns or less.

According to another embodiment of the present invention, the substrate may comprise a rigid magnetic disk, such as a computer data storage disk. Such disks require a thin film overcoat of a hard, wear resistant material to protect the disk from damage from head to disk contact during computer drive operation. Such a film may comprise at least one of a hydrogenated carbon, nitrogenated carbon and boron suboxide. The films can be deposited by sputtering or chemical vapor deposition. Preferably, the thin film thickness is 700 nm or less.

According to another embodiment of the present invention, the substrate may comprise a computer motherboard or a semiconductor package, and the film may comprise a metal lead which connects integrated circuit packages to each other and to various macrodevices on the motherboard.

Figure 7A:
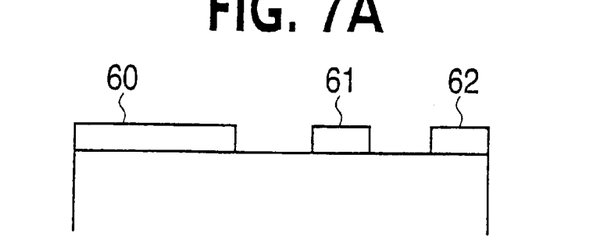
FIGS. 7A to 7D are cross sectional views of an adhesion strength measurement according to another embodiment of the present invention between two layers, and between a bottom layer and a substrate.
Figure 7B:
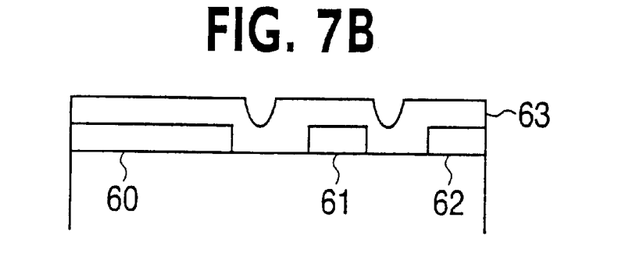
Figure 7C:
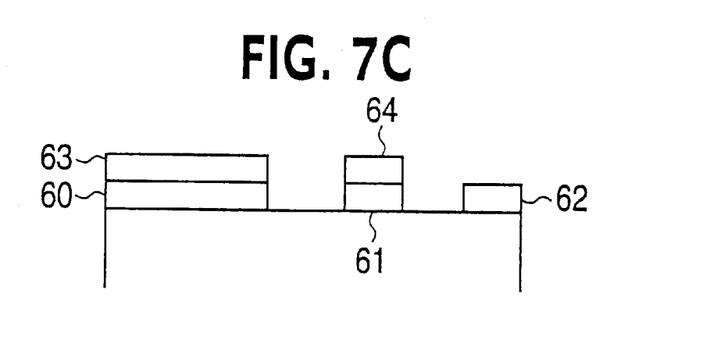
Figure 7D:
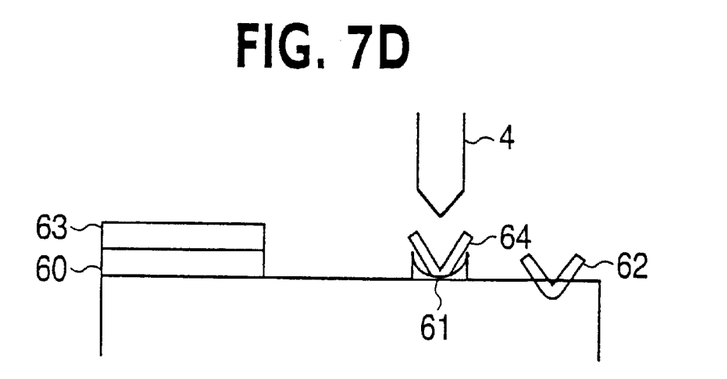

According to another embodiment of the present invention, the adhesion strength between two materials and between the bottom material and the substrate may be tested. This may occur, for example, when more than one hard metal gear box coating is deposited on a metal gear box or more than one layer is formed on a micromechanical device or magnetic disk substrate. In the case of an integrated circuit or a liquid crystal display, adhesion of two metal layers to each other and of the bottom metal layer to the underlying insulating layer may be tested. For example, a softer first layer, made of Al or any other suitable material, may be patterned to form a first main portion 60 and a second portion comprising two integrated test elements 61 and 62 over a substrate or an underlying layer, as shown in FIG. 7A. Then a harder second layer 63, such as a harder refractory metal or any other suitable material, may be deposited over the first patterned layer, as shown in FIG. 7B. The second layer may be patterned to leave a portion 64 covering the first test element 61 and to leave the second test element 62 exposed, as shown in FIG. 7C. Therefore, depth sensing indentation testing of both test elements 61/64 and 62 may be carried out sequentially to determine the adhesion strength of the first layer to the underlying substrate and the adhesion of the second layer 63 to the first layer 60 as shown in FIG. 7D.

As explained above, the integrated test element need not be separate from the rest of the thin film. For example, it is within the scope of the present invention that an edge of a contiguous thin film be used as the test element. In this case, only the edge near where the indenter tip is applied will delaminate. It should be understood that the method of this alternative embodiment is not limited to integrated circuit processing and may be used to make any device or article of manufacture that requires deposition of several layers, and may generally be used to test adhesion between various layers. The integrated test element may be formed concurrently with a thin film in any other application, such as a liquid crystal display, a Spindt cathode for emitting electrons from the cathode tip, a gear box, a micromechanical device and a magnetic disk, such as that in a disk drive.

Figure 8A:
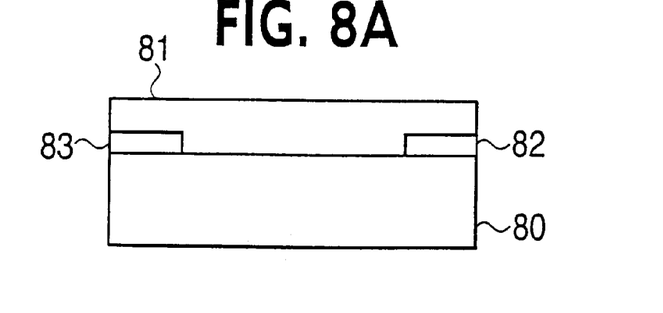
FIGS. 8A to 8D are cross sectional views of an adhesion strength measurement according to another embodiment of the present invention that utilizes sacrificial spacers.
Figure 8B:
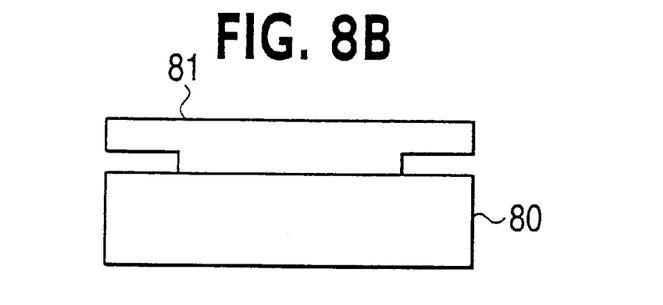
Figure 8C:
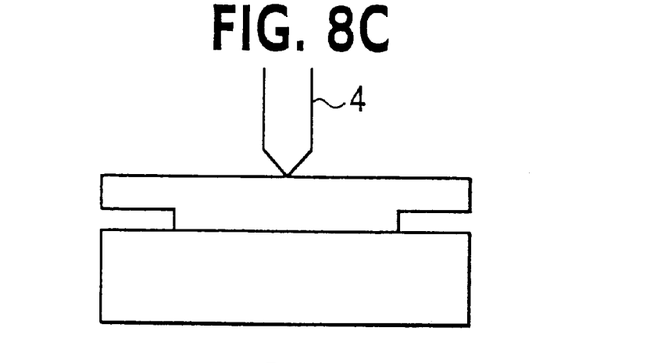
Figure 8D:
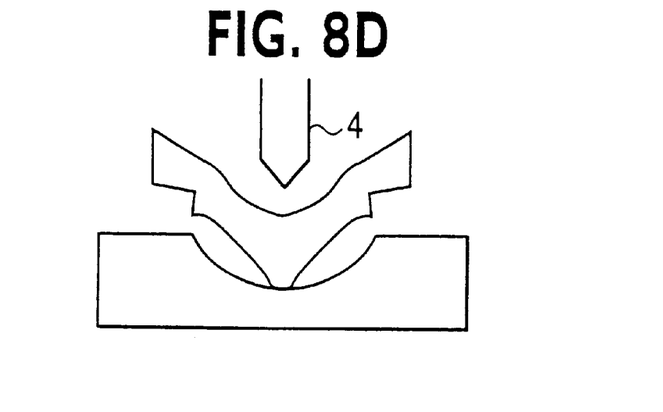

Another embodiment of the invention is shown in FIGS. 8A to 8D. In this embodiment, sacrificial spacers 82, 83 are used to enhance the delamination of the test element (or a thin film strip being tested) 81 from the substrate 80. The sacrificial spacers 82,83 are first formed on the substrate 80, as shown in FIG. 8A. Thus the test element 81 formed over the spacers 82,83 will be of a distorted "T" structure. The test element has a main portion in contact with the substrate and at least one wing portion in contact with the spacers but not with the substrate. The spacers are then selectively removed while leaving the test element substantially unchanged, as shown in FIG. 8B. The spacers may be removed by a selective etchant that etches the spacer material, but not the substrate or the test element material. For example, if the spacers comprise silicon nitride, the test element comprises aluminum, and the substrate comprises silicon dioxide, then an 85% phosphoric acid solution at 180° C. may be used to selectively etch away the spacers. Removal of the spacers leaves a crack at the interface between the substrate and the test element. Thus, when an indenter tip 4 is applied to the test element, as shown in FIGS. 8C and 8D, a smaller Mode I stress is necessary to enlarge a Mode I opening, because the beginning of the opening has already been created by the removal of the spacers. As may be readily seen in FIG. 8B, the wing portions of the test element are farther removed from the substrate than the main portion of the test element. The sacrificial spacers are especially useful in situations where the test element material has a very high adhesion strength to the substrate.

Alternatively, in lieu of the spacers 82 and 83, a razor blade edge can be inserted between the substrate 80 and the test element 81 to create a crack between the substrate and the test element. Furthermore, the crack between the substrate and the test element can be formed by depositing a film having a large intrinsic stress on top of the test element 81. The extra strain energy in the deposited film provides additional driving force to lift the edges of the test element 81 away from the substrate 80 to create a crack.

Figure 9:
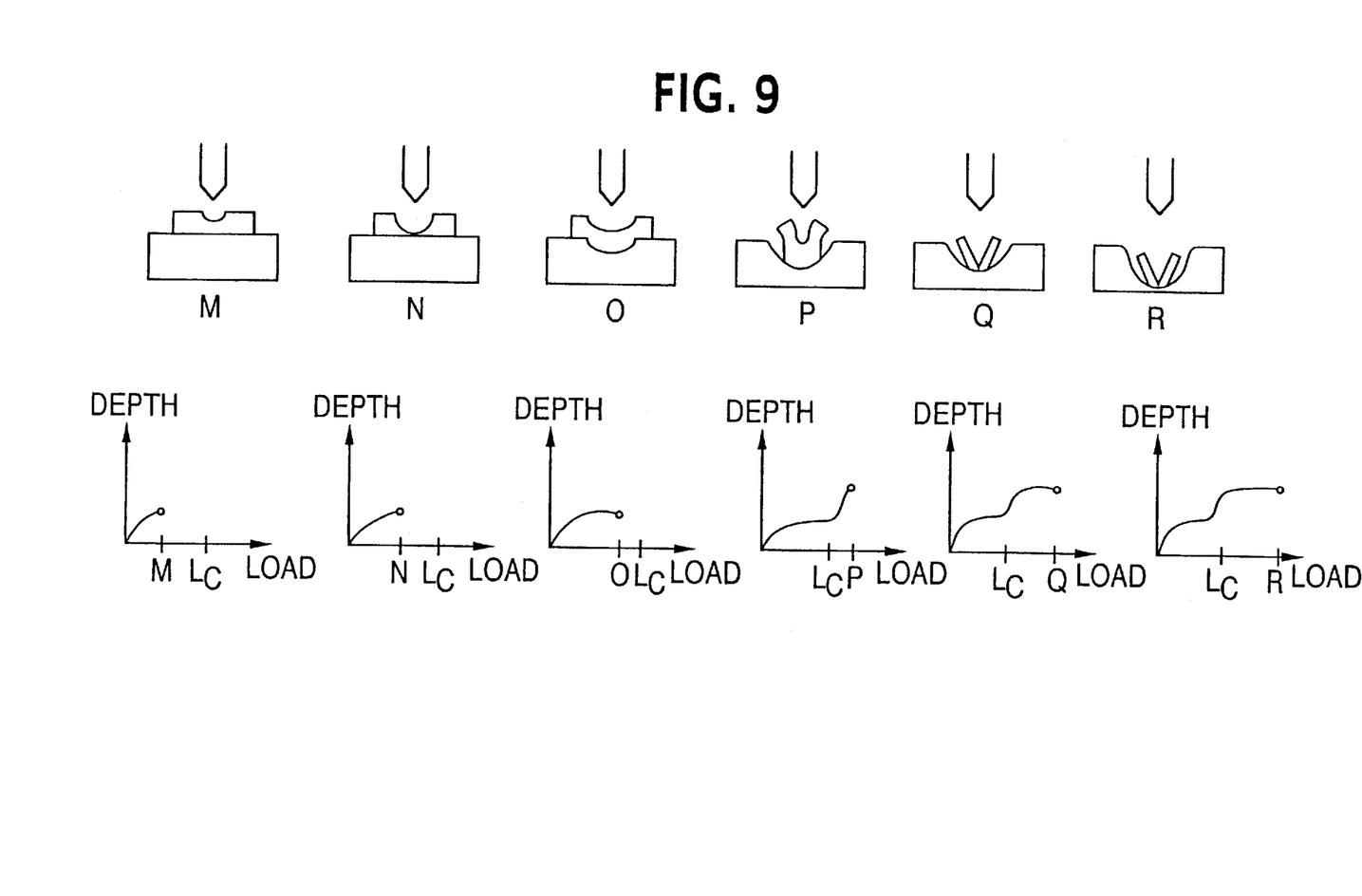
FIG. 9 is a cross sectional view of an adhesion strength-measurement according to another embodiment of the present invention that utilizes various loads on different test samples.

The adhesion strength of a film to a substrate may also be measured according to another embodiment of the present invention shown in FIG. 9. Thin film segments M, N, O, P, Q and R are formed on a substrate. The indenter tip is scanned from segment to segment by the oscillator 10 and the lock-in amplifier 11. A different, predetermined, constant load is then applied to each segment. The load is smallest on sample M and greatest on sample R. The range of the applied loads should be broad enough such that some loads (e.g. M, N and O) will be lesser than the critical load, $L_c$, while other loads (e.g. P, Q and R) will be greater than the critical load, $L_c$. The penetration depth of the indenter tip on each segment is then compared. On the segments that experience a load less than the critical (delaminating) load, $L_c$, the penetration depth will be significantly smaller than the penetration depth on the segments that experience a load greater than the critical load, $L_c$. The critical load value may then be estimated to be between the smallest load applied to a segment (P) having a relatively a large penetration depth and the largest load applied to a segment (O) having a relatively small penetration depth. In other words, the critical load, $L_C$, is a load between the load applied to sample P and the load applied to sample O, and may be calculated from the following formula:

$$L_C = (L_1 + L_2)/2$$

wherein $L_1$ is the greatest load applied to any segment which did not delaminate after the depth sensing indentation measurement, and $L_2$ is the least load applied to any segment which did delaminate after the depth sensing indentation measurement. The critical stress and interface strength may then be calculated from the estimated critical load. This approach is more useful when only estimates of strength are needed rather than very precise measurements.

While the invention has been described in detail and with reference to specific embodiments thereof, it will be apparent to one skilled in the art that various changes and modifications can be made therein without departing from the spirit and scope of the invention.

What is claimed is:

1. A method of determining adhesion strength between a first material and a second material, comprising:

forming a nanoindentation in at least the first material using an indenter tip;

monitoring at least one of
  a) a load applied to the indenter tip, and
  b) the penetration depth of the indenter tip; and calculating the adhesion strength between the first material and the second material based on at least one detected value of the load or at least one detected value of the penetration depth, wherein the first material is at least partially delaminated from the second material; and at least a part of the first material sinks in into the second material, wherein the first material is a thin film and the second material is a substrate, and wherein the thin film comprises a plurality of layers, and the substrate comprises one of a base material and at least one intermediate film formed on the base material.

2. A method of determining adhesion strength between a first material and a second material, comprising:

forming a nanoindentation in at least the first material using an indenter tip;

monitoring at least one of
  a) a load applied to the indenter tip, and
  b) the penetration depth of the indenter tip; and calculating the adhesion strength between the first material and the second material based on at least one detected value of the load or at least one detected value of the penetration depth, wherein the first material is at least partially delaminated from the second material; and at least a part of the first material sinks in into the second material, wherein the first material is a thin film and the second material is a substrate, and wherein the thin film comprises a first portion and a second portion, and wherein the first portion of the thin film is a test element.

3. The method of claim 2, wherein the second portion of the thin film comprises at least one of a metal film, an electrode for a semiconductor device, an interconnection for an integrated circuit or a liquid crystal display, a semiconductor device package lead, a gear box coating, a magnetic disk overcoat, an electron emissive cathode and a micromechanical device portion.

4. A method of determining adhesion strength between a first material and a second material, comprising:

forming a nanoindentation in at least the first material using an indenter tip;

monitoring at least one of
 a) a load applied to the indenter tip, and
 b) the penetration depth of the indenter tip; and calculating the adhesion strength between the first material and the second material based on at least one detected value of the load or at least one detected value of the penetration depth, wherein the step of monitoring the penetration depth of the indenter tip comprises monitoring the rate of change of the penetration depth of the indenter tip; and wherein the step of calculating the adhesion strength comprises calculating the adhesion strength between the first material and the second material based on at least one detected value of the rate of change of the penetration depth.

5. A method of using a nanoindentation apparatus, comprising:

placing an indenter tip in contact with a sample;

applying a variable load to the indenter tip;

monitoring a penetration depth of the indenter tip into the sample;

calculating adhesion strength of a first part of the sample to a second part of the sample based on at least one detected value of the variable load or at least one detected value of the penetration depth;

detecting a sudden change in the penetration depth rate; and detecting a critical value of the applied load at the time of the sudden change in the penetration depth rate.

6. The method of using the nanoindentation apparatus of claim 5, wherein the step of calculating adhesion strength of a first part of the sample to a second part of the sample comprises:

calculating a critical stress from the detected critical value of the applied load; and calculating the adhesion strength of a first part of the sample to a second part of the sample based on the calculated critical stress.

7. The method of using a nanoindentation apparatus of claim 5, wherein the applied variable load is a load that increases with time at a predetermined rate.

* * * * *